United States Patent
Miller

(10) Patent No.: US 10,366,462 B1
(45) Date of Patent: Jul. 30, 2019

(54) DRUG INTERACTION REVIEW METHODS AND SYSTEMS

(71) Applicant: Express Scripts, Inc., St. Louis, MO (US)

(72) Inventor: Steven B. Miller, St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 487 days.

(21) Appl. No.: 13/850,476

(22) Filed: Mar. 26, 2013

Related U.S. Application Data

(60) Provisional application No. 61/615,672, filed on Mar. 26, 2012.

(51) Int. Cl.
*G06Q 50/22* (2018.01)
*G06Q 10/06* (2012.01)

(52) U.S. Cl.
CPC ............. *G06Q 50/22* (2013.01); *G06Q 10/06* (2013.01)

(58) Field of Classification Search
CPC .... G06F 19/3456; G06F 19/322; G06F 11/00; G06Q 50/24; G06Q 50/22; G06Q 30/0607
USPC .............................................. 705/2, 3; 221/2
See application file for complete search history.

(56) References Cited

U.S. PATENT DOCUMENTS

| | | | | |
|---|---|---|---|---|
| 5,797,515 A * | 8/1998 | Liff | | G06F 19/3462 221/2 |
| 7,765,107 B2 * | 7/2010 | Reardan et al. | | 705/2 |
| 7,970,622 B2 * | 6/2011 | Lilly | | G06F 19/322 600/300 |
| 8,086,470 B2 * | 12/2011 | Siegel | | G06F 19/3456 705/2 |
| 8,335,697 B2 * | 12/2012 | Siegel | | G06F 19/3456 705/2 |
| 8,380,540 B1 * | 2/2013 | Smith | | G06F 19/328 705/3 |
| 8,548,824 B1 * | 10/2013 | daCosta et al. | | 705/3 |
| 8,626,529 B1 * | 1/2014 | Pinsonneault | | 705/2 |

(Continued)

FOREIGN PATENT DOCUMENTS

WO   WO 2007/133478 A2 * 12/2007

OTHER PUBLICATIONS

Google patents search, Jan. 3, 2017.*

(Continued)

*Primary Examiner* — Dilek B Cobanoglu
(74) *Attorney, Agent, or Firm* — Husch Blackwell LLP

(57) ABSTRACT

Methods and systems for drug interaction review are described. In an example embodiment, a prescription request is received for a prescription drug. The prescription drug is associated with a prescription. A determination that the prescription drug is a controlled substance is made. Pharmacy claims data is analyzed to determine whether past claims adjudication data is associated with a patient controlled substance identifier. The patient controlled substance identifier is associated with a patient that has been prescribed the prescription drug through the prescription without identifying the patient as being a member of a benefit manager. The prescription request is evaluated based on a determination that the past claims adjudication data is associated with the patient controlled substance identifier. A notification is generated based on evaluation of the prescription request. Additional methods and systems are disclosed.

17 Claims, 10 Drawing Sheets

(56) References Cited

U.S. PATENT DOCUMENTS

| | | | |
|---|---|---|---|
| 8,688,477 B1* | 4/2014 | Huizenga | 705/3 |
| 8,738,399 B1* | 5/2014 | Abou Nader et al. | 705/2 |
| 2002/0032582 A1* | 3/2002 | Feeney et al. | 705/2 |
| 2006/0074717 A1* | 4/2006 | Feldman | G06Q 30/02 705/3 |
| 2012/0046970 A1* | 2/2012 | Potts | G06F 19/3462 705/3 |
| 2012/0150563 A1* | 6/2012 | Carroll | G06Q 50/22 705/3 |
| 2013/0090947 A1* | 4/2013 | Nockley | G06F 19/3456 705/3 |
| 2014/0012600 A1* | 1/2014 | Domesek | G06F 19/3456 705/3 |
| 2014/0188498 A1* | 7/2014 | Petrimoulx | G06Q 30/0607 705/2 |

OTHER PUBLICATIONS

Google patents search, Aug. 4, 2017.*
Google patents search, May 25, 2018.*
Google search, May 25, 2018.*
Google patents search, Mar. 13, 2019.*

* cited by examiner

DRUG INTERACTION REVIEW METHODS AND SYSTEMS

CROSS-REFERENCE TO A RELATED APPLICATION

This application claims the benefit of U.S. provisional patent application 61/615,672, filed on 26 Mar. 2012, entitled "Drug Interaction Review Methods and Systems," the entire disclosure of which is incorporated herein by reference.

FIELD

The field relates to drug interaction review, and more particularly to drug interaction review performed on controlled substances.

BACKGROUND

Pharmacy benefit managers generally provide prescription drug programs for clients that may, for example, sponsor drug benefit programs for members. As part of the providing the prescription drug programs for clients, pharmacy benefit managers (PBM's) may adjudicate claims from pharmacies for prescriptions filled by members at various pharmacies. The PBM may also reimburse the pharmacies for prescriptions obtained by members at the pharmacies. The PBM may also bill clients for the cost of prescriptions adjudicated by the pharmacy benefit manager.

Narcotics may be prescribed to patents by doctors to treat pain. Narcotics may then be used, overused, or abused by the patients. Patients may also become addicted to the narcotics. Certain patients may not seek to have prescriptions of some or all of their narcotics filled through the use of their prescription drug programs. In other instances, patients may not have a prescription drug program through which they can receive a drug benefit.

DETAILED DESCRIPTION

Figure 1:
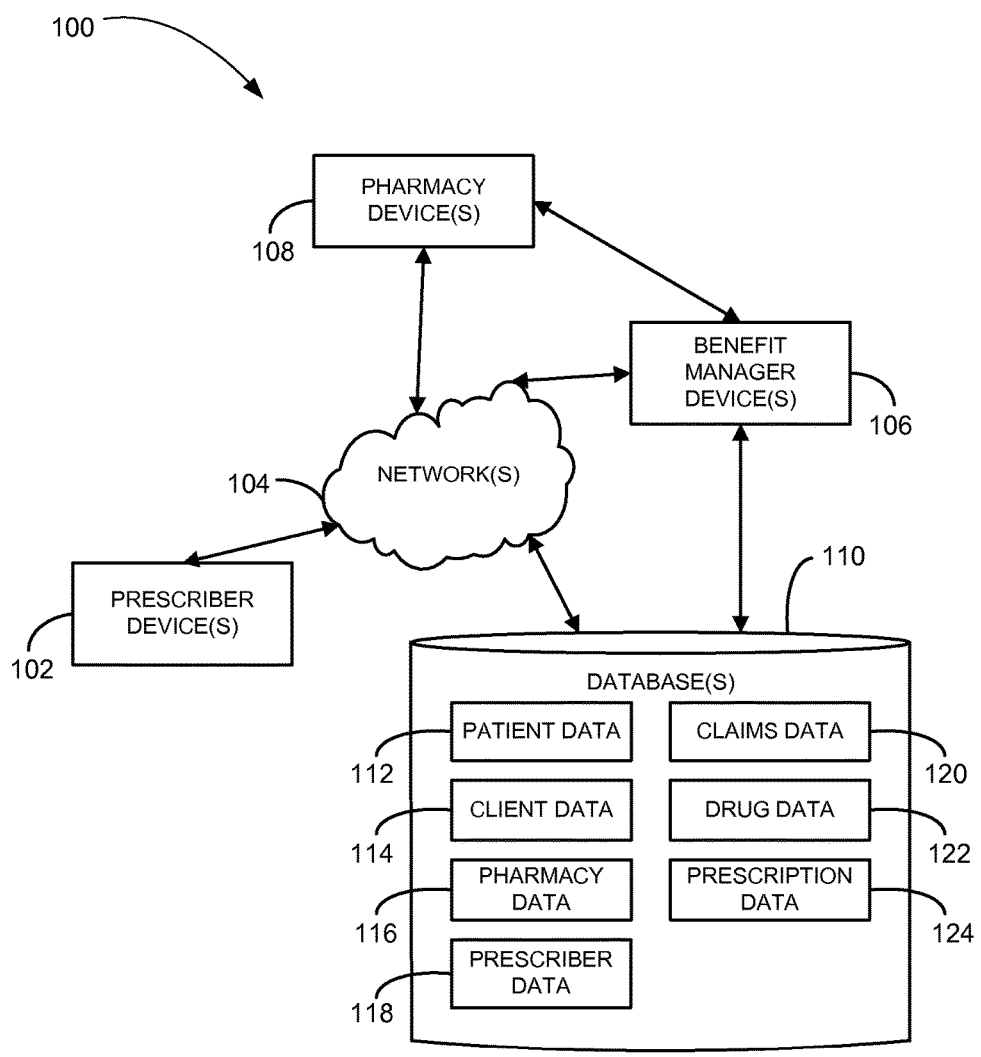
FIG. 1 is a block diagram of an example system, according to an example embodiment.

Example methods and systems for drug interaction review are described. In the following description, for purposes of explanation, numerous specific details are set forth in order to provide a thorough understanding of example embodiments. It will be evident, however, to one of ordinary skill in the art that embodiments of the invention may be practiced without these specific details.

Generally, a client engages a pharmacy benefit manager (PBM) to offer a drug benefit program to members. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. A person who is a participant or member of a drug benefit program offered by the client may obtain prescription drugs according to pricing, pharmacy selection, rebates, discounts and the like provided by the terms of the drug benefit program.

The client's offered drug benefit program may be a stand-alone drug benefit operated by the PBM, or as part of a health care benefit operated by a health insurance company where the PBM services are offered directly by the health insurance company or offered indirectly by the PBM on behalf of the health insurance company.

In some instances, a member of benefit manager may not wish to be identified as such. In addition, some patients of pharmacies are not members of a benefit manager. For the patients that are members who do not wish to be identified and for the patients that are not members, the methods and systems may be used to identify potential drug interactions between a drug being prescribed to the patient and prior and/or current prescriptions being taken and/or having been taken by the patient.

In some instances, this may occur when a patient of a pharmacy pays cash. The resulting claim (as such) may then be invisible to an adjudication system. In some embodiments, the pharmacist will not submit a claim associated with a prescription when payment for the prescription is made with cash.

Some or all of the foregoing patients may have been prescribed a controlled substance or narcotic. In some embodiments, narcotics include opioids, commonly morphine and heroin and their derivatives, such as hydrocodone. In some embodiments, narcotics include plant-based products such as opium and its derivatives morphine, codeine and heroin. In some embodiments, narcotics include synthetic narcotics such as methadone and pethidine, as well as *cannabis*, coca and cocaine.

In some embodiments, narcotic includes any of the following whether produced directly or indirectly by extraction from substances of vegetable origin or independently through chemical synthesis or by a combination of extraction and chemical synthesis:

Opium, opiates, derivatives of opium and opiates, including their isomers, esters, ethers, salts, and salts of isomers, esters, and ethers whenever the existence of such isomers, esters, ethers and salts is possible within the specific chemical designation. Such term does not include the isoquinoline alkaloids of opium.

Poppy straw and concentrate of poppy straw.

Coca leaves, except coca leaves and extracts of coca leaves from which cocaine, ecgonine and derivatives of ecgonine or their salts have been removed.

Cocaine, its salts, optical and geometric isomers, and salts of isomers.

Ecgonine, its derivatives, their salts, isomers and salts of isomers.

Any compound, mixture, or preparation which contains any quantity of any of the foregoing substances.

In some embodiments, the methods and systems may reduce narcotics abuse. In some embodiments, the methods and systems may prevent patient adverse reactions to certain drugs.

FIG. 1 is a block diagram of an example system 100, according to an example embodiment. The system 100 is an example environment in which a drug interaction review may be performed on behalf of a patient of a pharmacy. The system 100 includes a prescriber device 102 in communication with a benefit manager device 106 over a network 104.

The prescriber device 102 may be operated by, or on behalf of, a medical care professional or prescriber that may prescribe a course of treatment that may include a prescribed drug for a patient. In general, the medical care professional operating a prescriber device 102 is a person that is capable of writing a prescription or script for a medication. Examples of prescribers include doctors, nurse practitioners, and dentists. In some embodiments, the prescribers may be part of a physician network. For example, the physician network may be able to obtain legally valid scripts in one or more of the states or other geographic regions. The medical care professional may use the prescriber device 102 to review information received about a patient and approve the patient to have or otherwise receive an electronic script for a medication (e.g., a prescription drug). In general, the electronic script is for a particular member. However, in some embodiments the electronic script may be for a group of people (e.g., a member and the member's family). In some embodiments, the prescriber may provided the patient with a paper script instead of, or in addition to, the electronic script. The paper script may be provided with or without using the prescriber device 102. In some embodiments, the prescription is written electronically, in paper, or otherwise for a patient who is not a member of a prescription drug benefit.

In some embodiments, the prescriber device 102 may be utilized by the medical care professional to transmit a prescription associated with a patient (who may be a member of the drug benefit program) to a pharmacy (e.g., via the pharmacy device 108) and/or to the pharmacy benefit manager device 106. The pharmacy, to which the prescription may be transmitted, may be a retail pharmacy location, a mail order pharmacy, or another type of drug dispensing facility.

Examples of the prescriber device 102 include a set-top box (STB), a receiver card, a mobile telephone, a personal digital assistant (PDA), a display device, a portable gaming unit, and a computing system; however other devices may also be used. For example, the prescriber device 102 may include a mobile electronic device, such an IPHONE or IPAD device by Apple, Inc., mobile electronic devices powered by ANDROID by Google, Inc., and a BLACKBERRY device by Research In Motion Limited. The prescriber device 102 may also include other computing systems, such as desktop computing devices, notebook computing devices, netbook computing devices, gaming devices, and the like. Other types of electronic devices may also be used.

The prescriber device 102 may be associated with a single prescriber, or multiple prescribers. A prescriber may use a single prescriber device or multiple prescriber devices.

The network 104 by which the patient device 102 communicates with the benefit manager device 106, and/or the pharmacy device 108 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used. In some embodiments, the network 104 may include a prescribing network such as the electronic prescribing network operated by Surescripts of Arlington, Va.

The benefit manager device 106 is a device operated by an entity at least partially responsible for the management of a drug benefit program. The patient to whom the prescription is written by the prescriber (e.g., as may be operating the prescriber device 102) may be, or may not be, a member of a benefit manager that is capable of receiving a prescription drug benefit.

While the entity operating the benefit manager device 106 is typically a PBM, other entities may operate the benefit manager device 106 either on behalf of themselves, the PBM, or another entity. In some embodiments, a PBM that provides the drug benefit may also provide one or more than one additional benefits including a health benefit, a dental benefit, a vision benefit, a wellness benefit, a radiology benefit, a pet care benefit, an insurance benefit, a long term care benefit, a nursing home benefit, and the like.

Some of the operations of the PBM that operates the benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of the client with the PBM. The member's co-pay may be based on be a flat co-pay (e.g., $10), co-insurance (e.g., 10%), and/or a deductible (e.g., for first $500 of annual prescription drug spend) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing the formulary to determine appropriate co-pay, coinsurance, and deductible for the prescription drug, and performing a DUR on the member. The PBM then provides a response to the pharmacy following performance of the aforementioned operations. As part of the adjudication, the client (or the PBM on behalf of the client) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as part of the adjudication process.

The amount of reimbursement paid to the pharmacy by the client and/or member may be based at least in part on the type of pharmacy network in which the pharmacy is included. Other factors may be used to determine the reimbursement amount in addition to the type of pharmacy network. For example, if the member pays the pharmacy for the prescription without using the prescription drug benefit provided by the benefit manager, the amount of money paid by the member may be higher and the amount of money received by the pharmacy for dispensing the prescription drug and for the prescription drug itself may be higher.

The pharmacy device 108 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy device 108 may be utilized by the pharmacy to submit the claim to the PBM for adjudication. Additionally, in some embodiments, the pharmacy device 108 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some embodiments, the benefit manager 106 may track prescription drug fulfillment and/or other information for patients that are not members, or have not identified themselves as members, at the time (or in conjunction with the time) in which they seek to have a prescription filled at a pharmacy.

The benefit manager device 106 may be in a client-server relationship with the prescriber device 102 and/or the pharmacy device 108, a peer-to-peer relationship with the prescriber device 102 and/or the pharmacy device 108, or in a different type of relationship with the prescriber device 102 and/or the pharmacy device 108.

The benefit manager device 106 may be in communication directly (e.g., through local storage) and/or through the network 104 (e.g., in a cloud configuration or software-as-a-service) with a device that stores a database 110. The database 110 may be deployed on the prescriber device 102, the benefit manager device 106 or the pharmacy device 108, on the patient device 102, the benefit manager device 106 and the pharmacy device 108, at least partially on one or more of the patient device 102, the benefit manager device 106 and the pharmacy device 108, on a separate device, or may otherwise be deployed. The database 110 may store patient data 112, client data 114, pharmacy data 116, prescriber data 118, claims data 120, drug data 122, and/or prescription data 124.

The patient data 112 includes information regarding patients. In some embodiments, the patient data 112 includes information about the members associated with the benefit manager. Examples of the patient data 112 include name, address, telephone number, e-mail address, prescription drug history, and the like. The patient data 112 may include a client identifier that identifies the client associated with the member and/or a member identifier that identifies the member to the client.

In some embodiments, the patient data 112 includes information on medication use for respective patients and details of drug plan usage. The patient data 116 may include an identifier of the patient, the physician, and of the drug and a time of dosing of the drug.

In some embodiments, the patient data 112 of patients that have been identified as a member of the benefit manager may be maintained separately (e.g., in a separate database) from patients that have not been identified as a member. In some embodiments, the patient data 112 of patients that have paid cash for their prescription drug(s) may be maintained separately from patients that have not paid with cash for their prescription drug(s).

In some embodiments, the patient data 112 includes recordation of receipts of prescriptions that are associated with a controlled substance (e.g., for which a controlled substance has been prescribed) and/or recordation of member non-identifications. The member non-identification may reflect when patients have paid cash for fulfillment of their prescription drugs.

The client data 114 includes information regarding the clients of the benefit manager. Examples of the client data 114 include company name, company address, contact name, contact telephone number, contact e-mail address, and the like.

The pharmacy data 116 includes information regarding pharmacies. The pharmacy data 116 may include, by way of example, location data regarding the location of the pharmacies, information data regarding the pharmacy hours and/or telephone number, pharmacy network association data defining the pharmacy network associations of which the pharmacies are associated, and the like.

The prescriber data 118 includes information regarding prescribers. The prescriber data 118 may include, by way of example, location data regarding the location of the prescribers, information data regarding the prescriber hours and/or telephone number, prescriber network association data defining the prescriber network associations of which the prescribers are associated, and the like. The prescribers may be at a physician's office, a hospital, a location associated with a PBM, or the like.

The claims data 120 includes information regarding pharmacy claims adjudicated by the benefit manager. In some embodiments, the claims data 120 includes an identification of the client that sponsors the drug benefit program under which the claim is made, and/or the patient that purchased the prescription drug giving rise to the claim, the prescription drug that was filled by the pharmacy, and the price of the prescription drug provided under the drug benefit program. Additional information may be included.

In some embodiments, the claims data 120 does not directly identify the patient. Rather, at least portions of the claims data 120 may be associated with a patient controlled substance identifier. In some embodiments, the patient controlled substance identifier may be used to identify a patient that is receiving or has received a prescription drug, without identifying who the patient is.

The drug data 122 may include drug name (e.g., technical name and/or common name), other names by which the drug is known by, active ingredients, an image of the drug (e.g., in pill form), and the like. The drug data 122 may include information associated with a single medication or multiple medications.

The prescription data 124 includes information regarding prescriptions that may be issued by prescribers on behalf of patients, who may be members of the drug benefit plan, for example to be filled by a pharmacy. Examples of the prescription data 112 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.)

While the system 100 in FIG. 1 is shown to include single devices 102, 106, 108, multiple devices may be used. The devices 102, 106, 108 may be the same type of device or may be different device types. When multiple devices are present, the multiple devices may be of the same device type or may be of a different device type. Moreover, system 100 shows a single network; however, multiple networks can be used. The multiple networks may communicate in series with each other to link the devices 102, 106, 108 or in parallel to link the devices 102, 106, 108.

Figure 2:
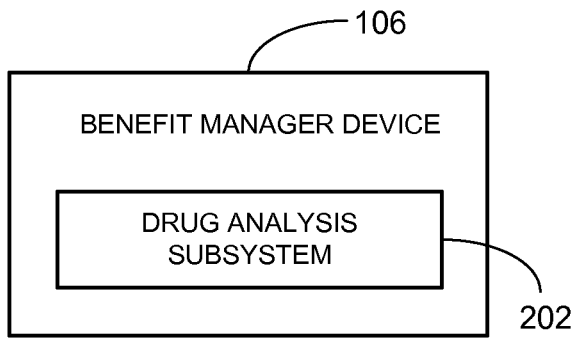
FIG. 2 is a block diagram of an example benefit manager device that may be deployed within the system of FIG. 1, according to an example embodiment.

FIG. 2 illustrates the benefit manager device 106, according to an example embodiment. The benefit manager device 106 may be deployed in the system 100, or may otherwise be used. The benefit manager device 106 may include the drug analysis subsystem 202. The drug analysis subsystem 202 may be used to perform a drug interaction review on a controlled substance for a patient.

Figure 3:
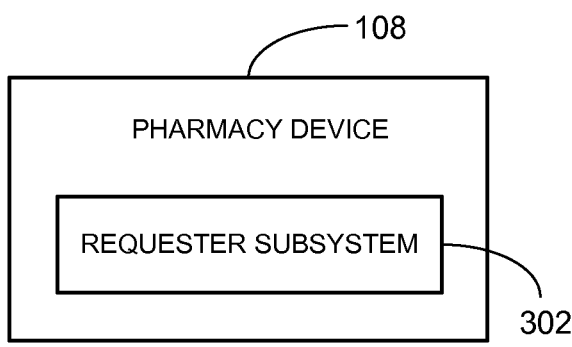
FIG. 3 is a block diagram of an example pharmacy device that may be deployed within the system of FIG. 1, according to an example embodiment.

FIG. 3 illustrates the pharmacy device 108, according to an example embodiment. The pharmacy device 108 may be deployed in the system 100, or may otherwise be used. The pharmacy device 108 may include the requester subsystem 302. The requester subsystem 302 may be used to transmit an adjudication request and receive a response to the adjudication request.

Figure 4:
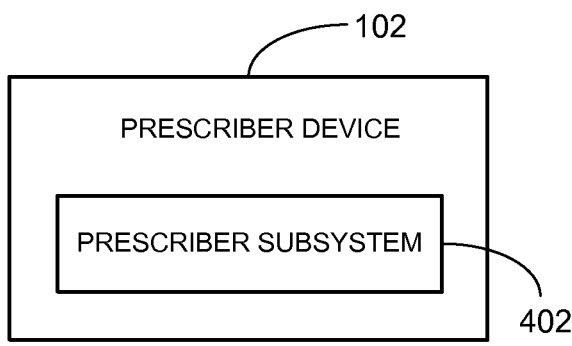
FIG. 4 is a block diagram of an example prescriber device that may be deployed within the system of FIG. 1, according to an example embodiment.

FIG. 4 illustrates the prescriber device 102, according to an example embodiment. The prescriber device 102 may be deployed in the system 100, or may otherwise be used. The prescriber device 102 may include the prescriber subsystem 402. The prescriber subsystem 402 may be used to receive drug interaction information associated with a patient.

Figure 5:
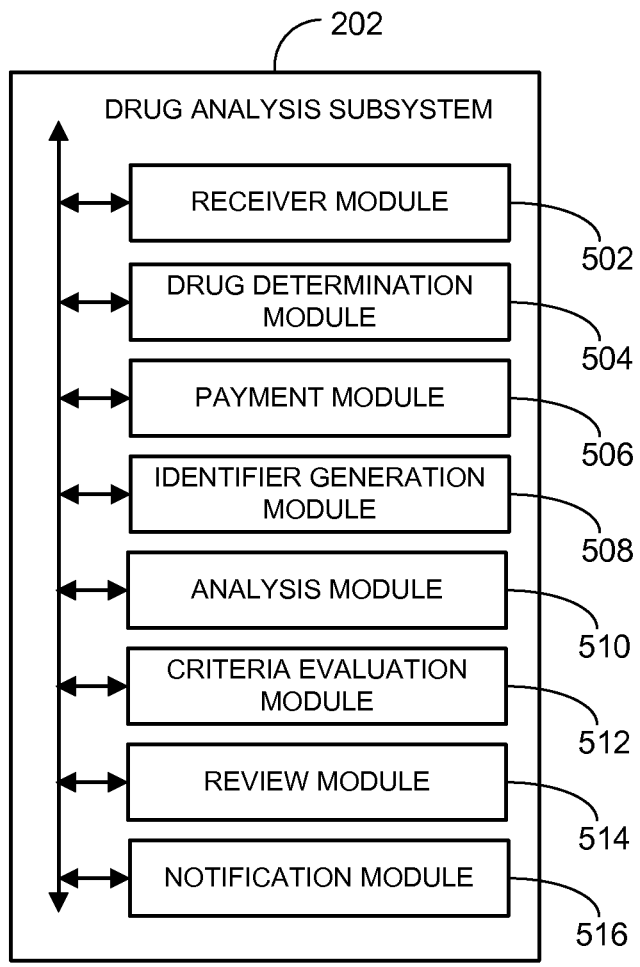
FIG. 5 is a block diagram of an example drug analysis subsystem that may be deployed within the benefit manager device of FIG. 2, according to an example embodiment.

FIG. 5 illustrates an example drug analysis subsystem 202 that may be deployed in the benefit manager device 106, or otherwise deployed in another system. One or more modules are communicatively coupled and included in the drug analysis subsystem 202 to perform a drug interaction review on a controlled substance for a patient. The modules of the drug analysis subsystem 202 that may be included are a receiver module 502, a drug determination module 504, a payment module 506, an identifier generation module 508, an analysis module 510, a criteria evaluation module 512, a review module 514, and a notification module 516. Other modules may also be included.

In some embodiments, the modules of the drug analysis subsystem 202 may be distributed so that some of the modules are deployed in the benefit manager device 106 and some modules are deployed in another device. In one embodiment, the modules are deployed in memory and executed by a processor coupled to the memory. The functionality contained within the modules 502-516 may be combined into a lesser number of modules, further divided among a greater number of modules, or redistributed among existing modules. Other configurations including the functionality of the modules 502-516 may be used.

The receiver module 502 receives a request associated with a prescription drug. In some embodiments, the request is an adjudication request for a prescription drug. The prescription drug is prescribed to the patient in a prescription. In general, the adjudication request includes a request to adjudicate a prescription drug claim for the prescription drug. The request may be for a single prescription drug associated with the prescription, or multiple prescription drugs associated with the prescription. The adjudication request may be received from the pharmacy device 108, from the prescriber device 102, or may otherwise be received.

Other kinds of requests may be received by the receiver module 502 such as a drug interaction request or a prescription fulfillment request. In general, the drug interaction request includes a request to determine whether the prescription drug associated with the prescription could cause an interaction with another prescription drug prescribed to the patient. In general, the prescription fulfillment request includes a request to fulfill the prescription.

A patient controlled substance identifier may be separately be received by the receiver module 502, or may be received as at least part of the request. In some embodiments, no patient controlled substance identifier is received by the receiver module 502.

In general, the patient controlled substance identifier is an identifier that is used to identify and/or track the patient being prescribed a prescription drug that is a controlled substance without associating the patient with a member identifier. In general, the member identifier is used to identify the patient as a member of a benefit manager. The patient controlled substance identifier, in some embodiments, is a different identifier than the member identifier associated with the patient.

In some embodiments, the drug determination module 504 determines that that the prescription drug identified in the request is a controlled substance or narcotic. The drug determination may be made when the patient controlled substance identifier is not received by the receiver module 502.

The payment module 506 may be deployed in the drug analysis subsystem 202 to determine that the adjudication request is associated with a cash purchase of the prescription drug. In some embodiments, the cash purchase by the patient may not enable the pharmacy, the benefit manager, or both the pharmacy and the benefit manger to identify the patient as being a member and/or track the prescription drugs being taken by the patient through a member identifier.

In some embodiments, the payment module 506 selects a cash purchase claims adjudication database among multiple available databases 110 based on a determination that the adjudication request is associated with the cash purchase. The cash purchase claims adjudication database may be maintained by the benefit manager and/or pharmacy separately from a database associated with patients (e.g., a member database).

The identifier generation module 508 generates the controlled substance identifier. The controlled substance identifier may be generated when not already received by the receiver module 502. In some embodiments, the controlled substance identifier is not provided to or known by the patient. In some embodiments, the controlled substance identifier is provided to and/or known by the patient.

The generation of the controlled substance identifier may be based on a prescriber associated with the prescription, a pharmacist associated with the prescription, a pharmacy associated with the prescription, a cash identifier associated with the prescription, a timing associated with the prescription, or the like. The controlled substance identifier may be generated when the prescriber is flagged, based on a likelihood of potential fraud associated with the prescribing of the controlled substance to the patient for filling at the pharmacy, a type of the doctor relative to the prescribed controlled substance, and the like.

The analysis module 510, when deployed, analyzes the claims data 120 to determine whether past claims data 120 is associated with a patient controlled substance identifier. By performing the analysis, the analysis module 510 may determine that the patient has previously been prescribed prescription drugs that may include controlled substances and/or non-controlled substances. Such determination may be made without use of a member identifier. The analysis of the claims data 120 may be performed by used of data modeling or the like. In some embodiments, the analysis of the claim data 120 is performed in response to generation of the controlled substance identifier and/or to a determination that the adjudication request is associated with a cash purchase.

In some embodiments, analyzing the pharmacy claims data includes selecting the past claims data 120 from the pharmacy claims data 120 based on a time criterion and analyzing the pharmacy claims data 120 to determine whether the past claims data 120 is associated with the patient controlled substance identifier. In general, a time criterion is a period of time over which the pharmacy claims data 120 is to be analyzed. The time criterion may be set by the benefit manager, the client, the benefit manager and the client, or otherwise. The time criterion may be designated so as to only review potentially current prescriptions associated with the patient, recent and current prescriptions associated with the patient, or otherwise.

The criteria evaluation module 512, when deployed, determines whether the prescription meets controlled substance criteria. In general, the controlled substance criteria is used to determine that the prescription drug is a controlled substance and the patient has not provided a member identifier that identifies the member as being a member of a benefit manager. The patient may have refused to provide an identifier (e.g., a member identifier), provided a controlled substance identifier, claimed not to have or know a member identifier, actually does not have a member identifier, provided a false member identifier, or the like.

The review module 514 performs a drug interaction review for the prescription drug. The drug interaction review may review potential interactions with the drug associated with the prescription and other know drugs that have been prescribed to the patient. In some embodiments, the drug interaction review is a prospective DUR. In some embodiments, the drug interaction review may include addressing one or more than one of the following: drug-disease contraindications, therapeutic interchange, generic substitution, incorrect drug dosage, inappropriate duration of drug treatment, drug-allergy interactions, and clinical abuse/misuse.

In some embodiments, the drug interaction review is based on the past claims adjudication data 120. In some embodiments, the drug interaction review is based on a determination that the prescription meets the controlled substance criteria.

The performance of the drug interaction review may be performed as part of performance of performing a drug utilization review (DUR) for the prescription drug based on the past claims adjudication data 120. In general, DUR may be used to ensure that prescriptions for outpatient drugs are appropriate, medically necessary, and not likely to result in adverse medical consequences. DURs may involve a comprehensive review of patients' prescription and medication data before, during, and after dispensing to ensure appropriate medication decision making and positive patient outcomes.

In some embodiments, the review module 514 identifies a past prescription associated with the past claims adjudication data 120. Performance of the drug interaction review for the prescription drug may then be based on the past prescription.

In some embodiments, the past claims adjudication data 120 does not identify (or specifically identify) the patient. In some embodiments, the past claims adjudication data 120 is associated with the patient controlled substance identifier. Thus, by use of the patient controlled substance identifier, and not a member identifier or other association of past claims data with the patient, the patient may be linked to past claims data.

The notification module 516 generates a notification based on performance of the drug interaction review by the review module 514. In some embodiments, the notification includes an amount to be paid to a pharmacy. The amount may be due by the patient to the pharmacy for receipt of the controlled substance.

In some embodiments, the notification module 516 transmits a response. The response may be based on the notification, may include the notification, or otherwise. The response may be provided to the same device that transmitted the adjudication request, or may be provided to a different device. The response may provide information requested through the request received by the receiver module 502.

The response may be to approve or disapproved the dispensing of the prescription drug. For example, the response to disapprove the dispensing drug may be based on a determination that the patient has recently obtained a controlled substance and that, in some instances, such requested usage is a violation of one or more than one applicable law.

In some embodiments, the payment module 506 records payment to a pharmacy. The recordation may be based on receipt of the adjudication request, performance of the drug interaction review, or may otherwise be made.

Figure 6:
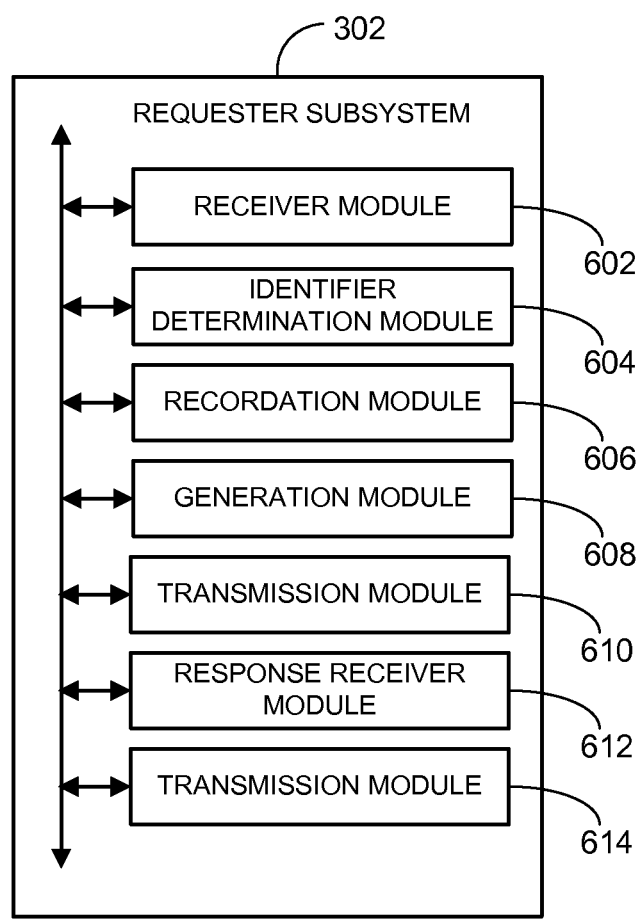
FIG. 6 is a block diagram of an example requester subsystem that may be deployed within the pharmacy device of FIG. 3, according to an example embodiment.

FIG. 6 illustrates a requester subsystem 302 that may be deployed in the pharmacy device 108, or otherwise deployed in another system. One or more modules are communicatively coupled and included in the requester subsystem 302 to transmit an adjudication request and receive a response to the adjudication request. The modules of the requester subsystem 302 that may be included are a receiver module 602, an identifier determination module 604, a recordation module 606, a generation module 608, a transmission module 610, a response receiver module 612, and a transmission module 614. Other modules may also be included.

In some embodiments, the modules of the requester subsystem 302 may be distributed so that some of the modules are deployed in the pharmacy device 108 and some modules are deployed in another device. In one embodiment, the modules are deployed in memory and executed by a processor coupled to the memory. The functionality contained within the modules 602-614 may be combined into a lesser number of modules, further divided among a greater number of modules, or redistributed among existing modules. Other configurations including the functionality of the modules 602-614 may be used.

In some embodiments, the receiver module 602 receives a member identifier and the identifier determination module 604 determines that the member identifier is not associated with the patient. The provided member identifier may be erroneously provided by the patient, purposely provided as a false identifier by the member, or otherwise. The member identifier may be received through a user interface available to a pharmacist technician, through a device (e.g., a mobile electronic device or kiosk) available to the patient, or may otherwise be received.

In some embodiments, the receiver module 602 receives a patient controlled substance identifier. The patient controlled substance identifier may be received from the patient (e.g., directly or through a device associated with the patient), from the benefit manager device 106, or otherwise.

In some embodiments, the receiver module 602 receives a transmission of the prescription from the prescriber device 102. The prescription may be received on the request of the pharmacy, may be provided in advance by the prescriber through the transmission, or otherwise. In some embodiments, the receiver module 602 receives prescription data through a user interface. The received prescription data may be data that is used to create an electronic record of the prescription for the patient. In some embodiments, the prescription includes a controlled substance that has been prescribed by a prescriber for the patient.

The recordation module 606 records receipt of a prescription associated with a controlled substance and records member non-identification. The non-identification may be recorded in a database or otherwise. In some embodiments, the member non-identification reflects that a patient associated with the prescription is not being identified as being a member of a benefit manager. In some embodiments, the member non-identification reflects that a member identifier has not been provided (e.g., by the patient). In some embodiments, the recordation of the member non-identification is based on a determination that the member identifier is not associated with the patient (e.g., through error or purposeful deception). The recordation of receipt of the prescription may be based on receipt of the transmission and/or receipt of the prescription data. In some embodiments, the member non-identification further reflects that the patient is paying for the prescription with cash.

In some embodiments, the generation module 608 generates a patient controlled substance identifier in response to recordation of member non-identification. The patient controlled substance identifier may be generated by the generation module 608 when not received by the receiver module 602. In some embodiments, generation may include utilizing a hash function on at least patient information associated with the patient to generate the patient controlled substance identifier. In some embodiments, the generation may be based on prescriber identification in response to recordation of member non-identification.

In some embodiments, generation of the patient controlled substance identifier is further based on timing associated with fulfillment of the prescription. The timing may be the date prescribed by the prescriber, the date the prescription is provided to the pharmacy, the renewal date of the prescription, or the like.

In some embodiments, generation of the patient controlled substance identifier is further based on a pharmacy location associated with fulfillment of the prescription, a pharmacy association associated with the fulfillment of the prescription, or both the pharmacy location and the pharmacy association.

The transmission module 610 transmits an adjudication request for the controlled substance based on recordation of the member non-identification. The adjudication request may be made prior to, drug, and/or after the prescription drug is dispensed to the patient. In some embodiments, the adjudication request may include the patient controlled substance identifier. The adjudication request may be transmitted to the benefit manager device 106 or to a different device.

The response receiver module 612 receives a response to transmission of the adjudication request. The response may include payment information, drug interaction notification, dispensing approval, or the like. The notification may be received from the benefit manager device 106 or from a different device.

The transmission module 614 transmits a payment request based on receipt of the response. The transmitted payment request may be made to the benefit manager device 106, a device associated with the client, or may otherwise be made.

Figure 7:
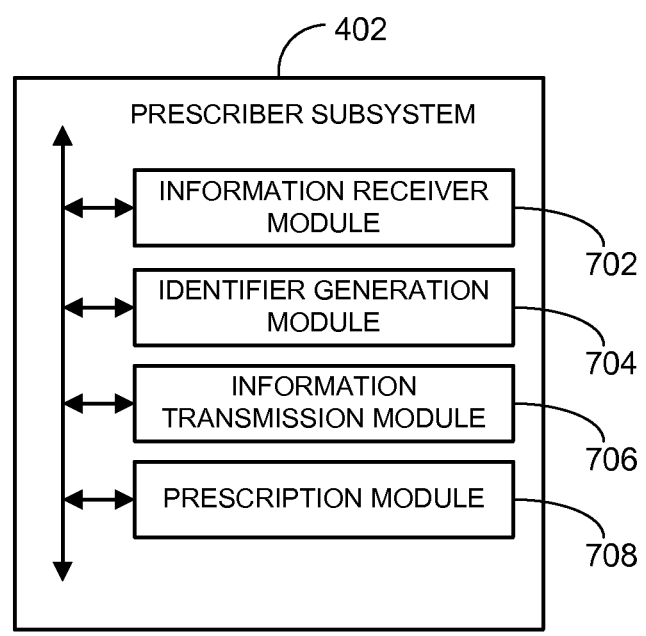
FIG. 7 is a block diagram of an example prescriber subsystem that may be deployed within the prescriber device of FIG. 4, according to an example embodiment.

FIG. 7 illustrates a prescriber subsystem 402 that may be deployed in the mobile electronic device 102, the benefit manager device 106, the pharmacy device 108, or otherwise deployed in another system. One or more modules are communicatively coupled and included in the prescriber subsystem 402 to receive drug interaction information associated with a patient. The modules of the prescriber subsystem 402 that may be included are an information receiver module 702, an identifier generation module 704, an information transmission module 706, and a prescription module 708. Other modules may also be included.

In some embodiments, the modules of the prescriber subsystem 402 may be distributed so that some of the modules are deployed in the prescriber device 102 and some modules are deployed in another device. In one embodiment, the modules are deployed in memory and executed by a processor coupled to the memory. The functionality contained within the modules 702-708 may be combined into a lesser number of modules, further divided among a greater number of modules, or redistributed among existing modules. Other configurations including the functionality of the modules 702-708 may be used.

In some embodiments, the information receiver module 702 receives the prescription information including selection of a controlled substance through a user interface. The prescription information may be provided through the user interface by a doctor, a physician's assistant, a nurse, or the like.

The identifier generation module 704 generates a patient controlled substance identifier based on patient information associated with the patient.

The information transmission module 706 transmits prescription information including selection of a controlled substance for a patient. The prescription information may be transmitted to the benefit manager device 106, the pharmacy device 108, both the benefit manager device 106 and the pharmacy device 108, or otherwise. In general, the prescription information does not include a member identifier that identifies the patient as being a member of a benefit plan provided through a benefit manager. In some embodiments, transmission of the prescription information by the information transmission module 706 is in response to receipt of the prescription information by the information receiver module 702. In some embodiments, the transmitted information may include the patient controlled substance identifier.

The information receiver module 702 receives drug interaction information associated with the patient in response to transmission of the prescription information. The drug interaction information may be received from the benefit manager device 106, the pharmacy device 108, both the benefit manager device 106 and the pharmacy device 108, or otherwise. The received drug interaction information may not be based on identification of the patient as being a member of the benefit plan provided through the benefit manager.

The prescription module 708 generates an electronic prescription for the patient based on receipt of the drug interaction information. In some embodiments, the prescription module 708 transmits the electronic prescription to the pharmacy device 108, the benefit manager device 106, or otherwise.

Figure 8:
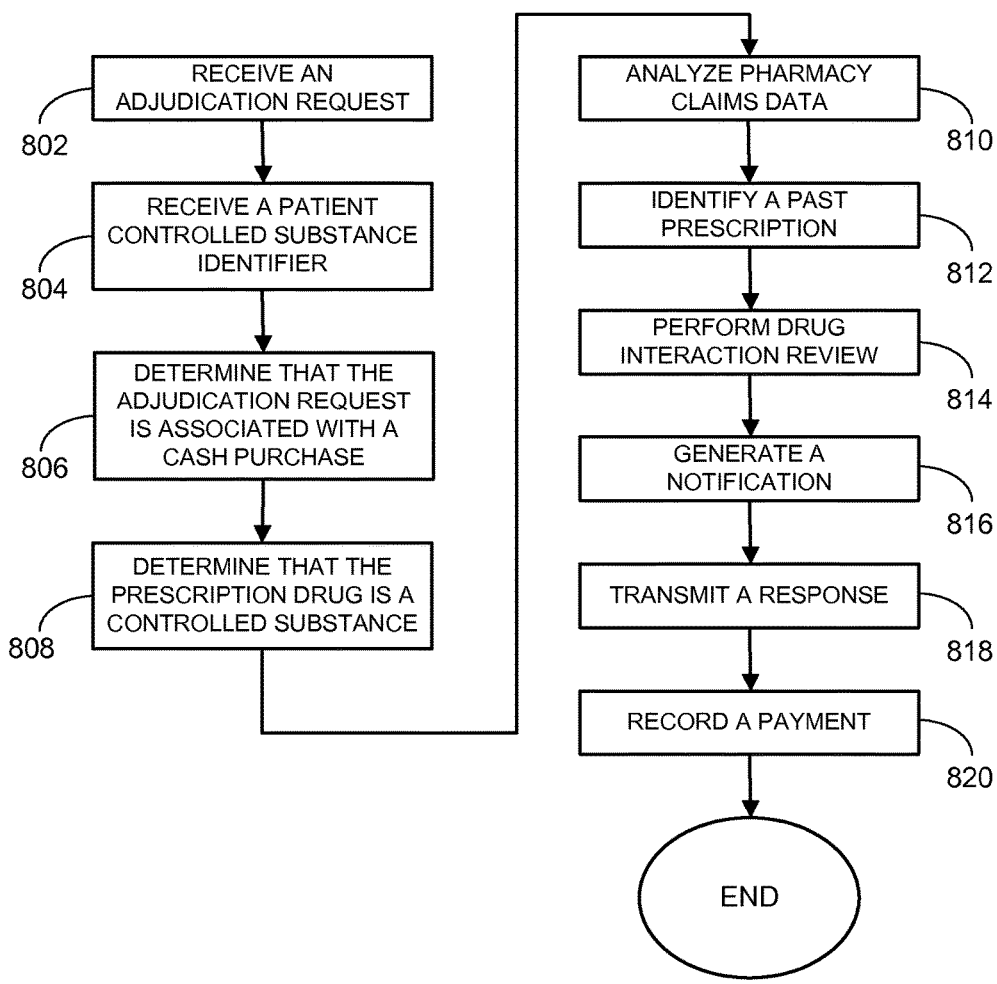
FIGS. 8 and 9 are example process flows illustrating methods for performing drug interaction reviews, according to example embodiments.

FIG. 8 illustrates a method 800 for performing a drug interaction review, according to an example embodiment. The method 800 may be performed by the benefit manager device 106, or may be otherwise performed.

A request associated with a prescription drug is received at block 802. The request may be an adjudication request, a drug interface request, a prescription fulfillment request, or the like. The prescription drug is associated with a prescription. In some embodiments, the patient controlled substance identifier is received during the operations performed at block 802. The patient controlled substance identifier may be included within the request or separate from the request. The request may be received from the prescriber device 102, the pharmacy device 108, or otherwise received.

A determination that the adjudication request is associated with a cash purchase of the prescription drug may be made at block 804. In some embodiments, a cash purchase claims adjudication database may be selected among available databases based on a determination that the adjudication request is associated with the cash purchase. A determination that that the prescription drug is a controlled substance may be made at block 806. The controlled substance identifier may be generated at block 808.

The pharmacy claims data 120 is analyzed at block 810 to determine whether past claims data is associated with a patient controlled substance identifier. In some embodiments, the analysis of the pharmacy claim data 120 is performed in response to generation of the controlled substance identifier.

In some embodiments, analyzing the pharmacy claims data 120 includes selecting the past claims data from the pharmacy claims data based on a time criterion and analyzing the pharmacy claims data to determine whether the past claims data is associated with the patient controlled substance identifier. A past prescription associated with the past claims adjudication data may be identified at block 812.

A drug interaction review is performed for the prescription drug at block 814 based on the past claims adjudication data. In some embodiments, the drug interaction review may be performed using the drug data 122 to determine interactions between the prescription drug and other prescription drugs previously and/or currently taken by the patient. In some embodiments, analyzing the pharmacy claim is in response to a determination that the adjudication request is associated with the cash purchase. Performance of the drug interaction review for the prescription drug may be based on the past prescription.

A notification is generated at block 816 based on performance of the drug interaction review. A response may be transmitted at block 818 based on the notification.

A payment to a pharmacy may be recorded at block 820. The recordation may be made based on receipt of the adjudication request or may otherwise be made.

Figure 9:
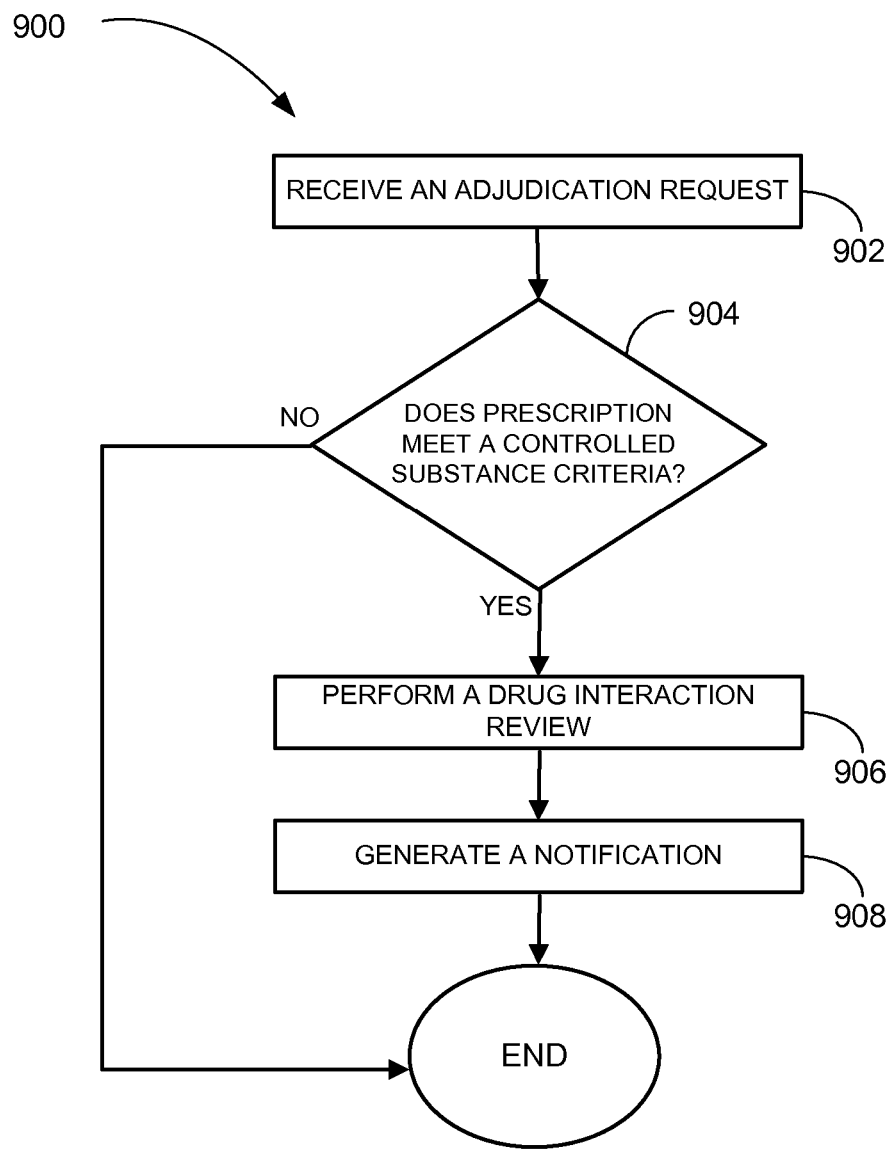

FIG. 9 illustrates a method 900 for performing a drug interaction review, according to an example embodiment. The method 900 may be performed by the benefit manager device 106, or may be otherwise performed.

A request is received for a prescription drug at block 902. The request may be an adjudication request, a drug interaction request, or the like. A determination whether the prescription meets a controlled substance criteria is performed at decision block 904. The controlled substance criteria including that the prescription drug is a controlled substance and the patient has not provided a member identifier that identifies the member as being a member of a benefit manager.

If a determination is made the prescription does not meet the controlled substance criteria, the method 900 may terminate. If a determination is made at decision block 904 that the prescription meets the controlled substance criteria, a drug interaction review for the prescription drug is performed at block 906 based on a determination that the prescription meets the controlled substance criteria.

A notification is generated at block 908 based on performance of the drug interaction review.

Figure 10:
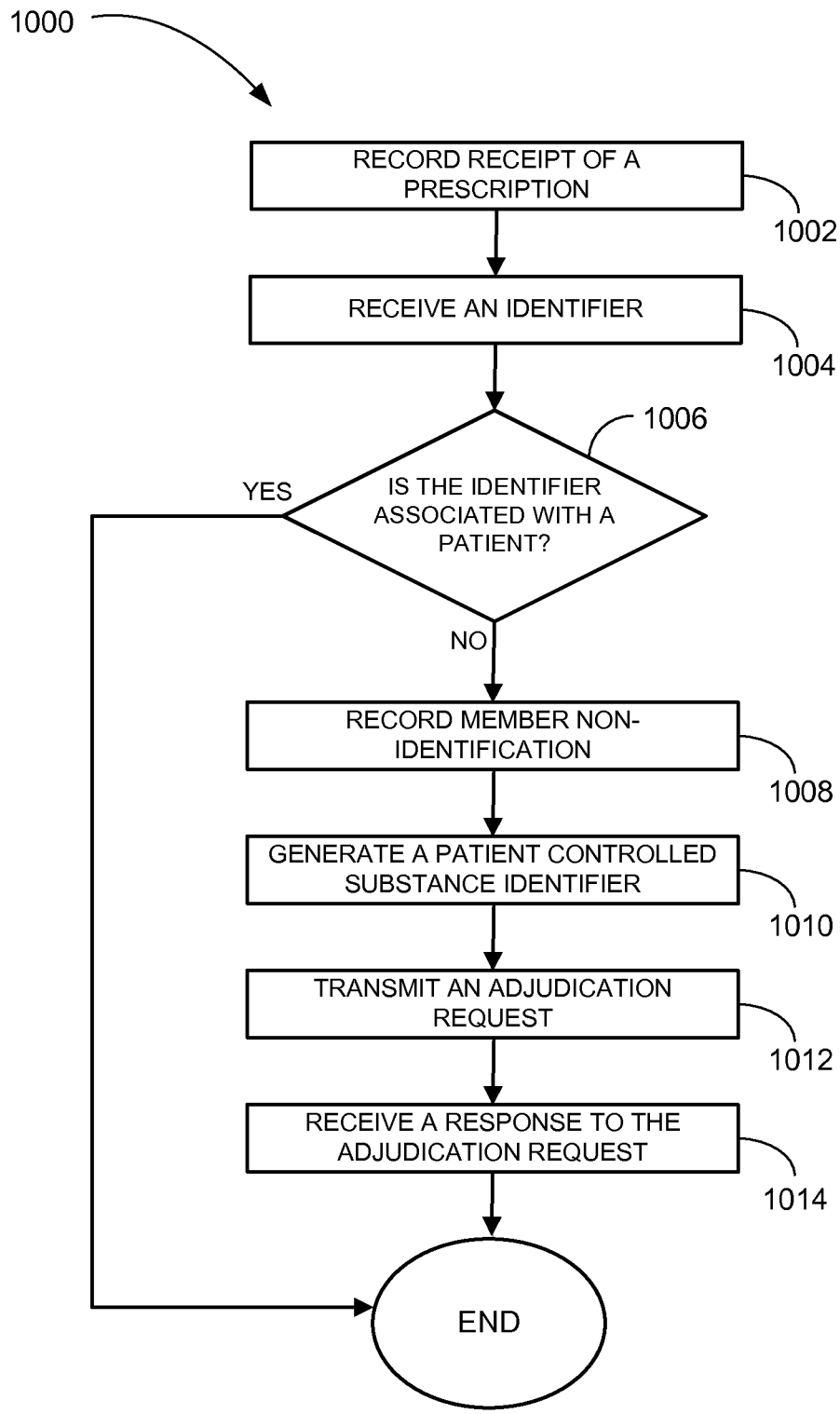
FIG. 10 is an example process flow illustrating a method for transmitting an adjudication request and receiving a response, according to an example embodiment.

FIG. 10 illustrates a method 1000 for transmitting an adjudication request and receiving a response, according to an example embodiment. The method 1000 may be performed by the pharmacy device 108, or may be otherwise performed.

Receipt of a prescription associated with a controlled substance is recorded at block 1002.

In some embodiments, a transmission of the prescription from the prescriber device 102 is received and the recordation of receipt of the prescription is based on receipt of the transmission. In some embodiments, prescription data is received through a user interface and recordation of receipt of the prescription is based on receipt of the prescription data.

In some embodiments, an identifier is received at block 1004. In some embodiments, the identifier received at block 1004 is a patient controlled substance identifier.

A determination may then be made at decision block 1006 as to whether the identifier is associated with the patient. If a determination is made that the identifier is associated with the patient, the method 1000 may terminate. For example, if the identifier provided is the member identifier associated with the patient. If a determination is made at decision block 1006 that the identifier is not associated with the patient, member non-identification is recorded at block 1008. The member non-identification reflects that a patient associated with the prescription is not being identified as being a member of a benefit manager.

In some embodiments, a patient controlled substance identifier is generated at block 1010 in response to recordation of member non-identification. Generation of the patient controller may be further based on timing associated with fulfillment of the prescription, a pharmacy location associated with fulfillment of the prescription, a pharmacy association associated with the fulfillment of the prescription, or the like.

In some embodiments, generation of the patient controller identifier includes utilizing a hash function on at least patient information associated with the patient to generate the patient controlled substance identifier. In some embodiments, generation of the patient controller identifier includes generating the patient controlled substance identifier based on prescriber identification in response to recordation of member non-identification.

An adjudication request is transmitted for the controlled substance at block 1012 based on recordation of the member non-identification. A response to transmission of the adjudication request is received at block 1014. A payment request may be transmitted at block 1016 based on receipt of the response.

Figure 11:
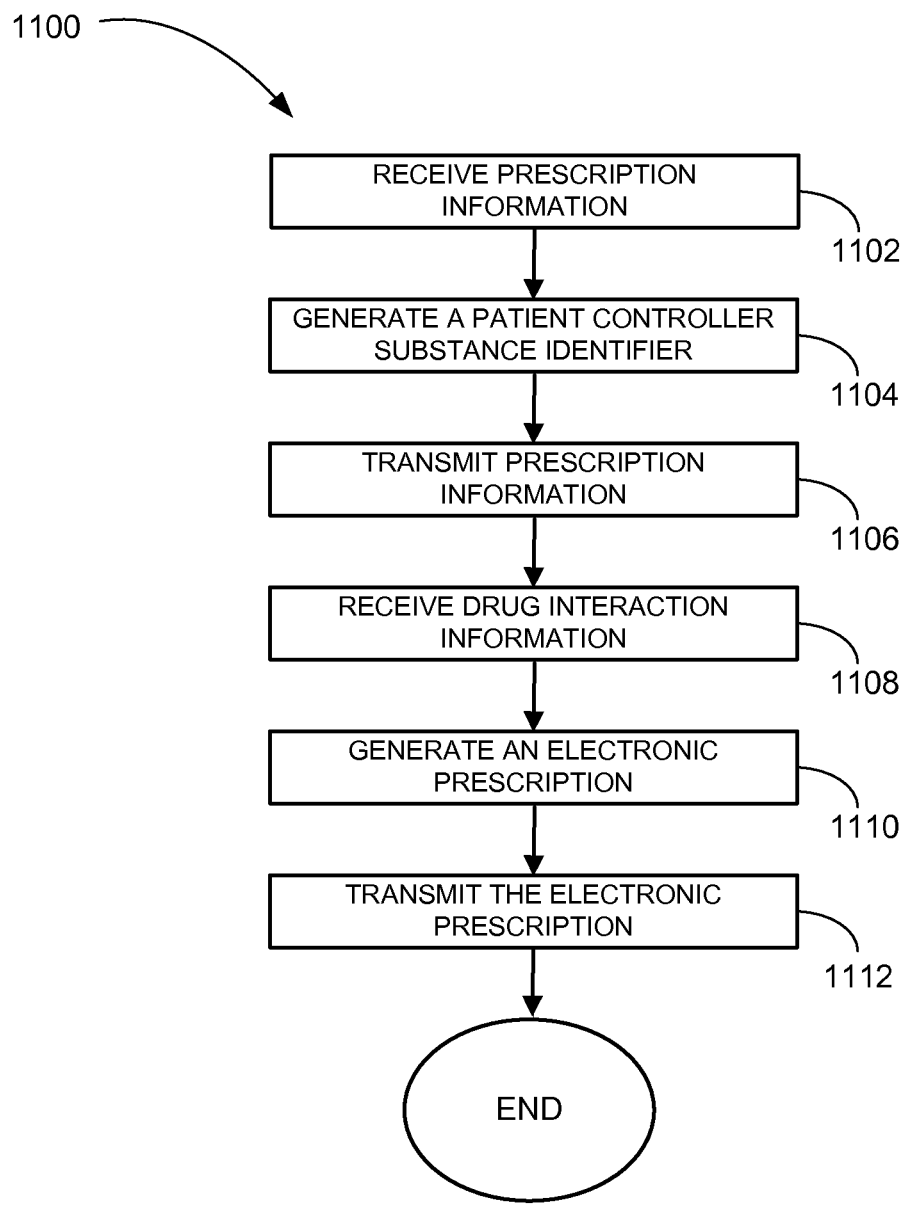
FIG. 11 is an example process flow illustrating a method for receiving drug interaction information associated with a patient, according to an example embodiment.

FIG. 11 illustrates a method 1100 for receiving drug interaction information associated with a patient, according to an example embodiment. The method 1100 may be performed by the prescriber device 102, or may be otherwise performed.

At block 1102, the prescription information including selection of a controlled substance may be received through a user interface.

A patient controlled substance identifier may be generated at block 1104 based on patient information associated with the patient.

Prescription information including selection of a controlled substance for a patient is transmitted at block 1106. Drug interaction information associated with the patient is received at block 1108 in response to transmission of the prescription information.

An electronic prescription may be generated for the patient at block 1110 based on receipt of the drug interaction information. The electronic prescription may be transmitted to the pharmacy device 108 at block 1112.

Figure 12:
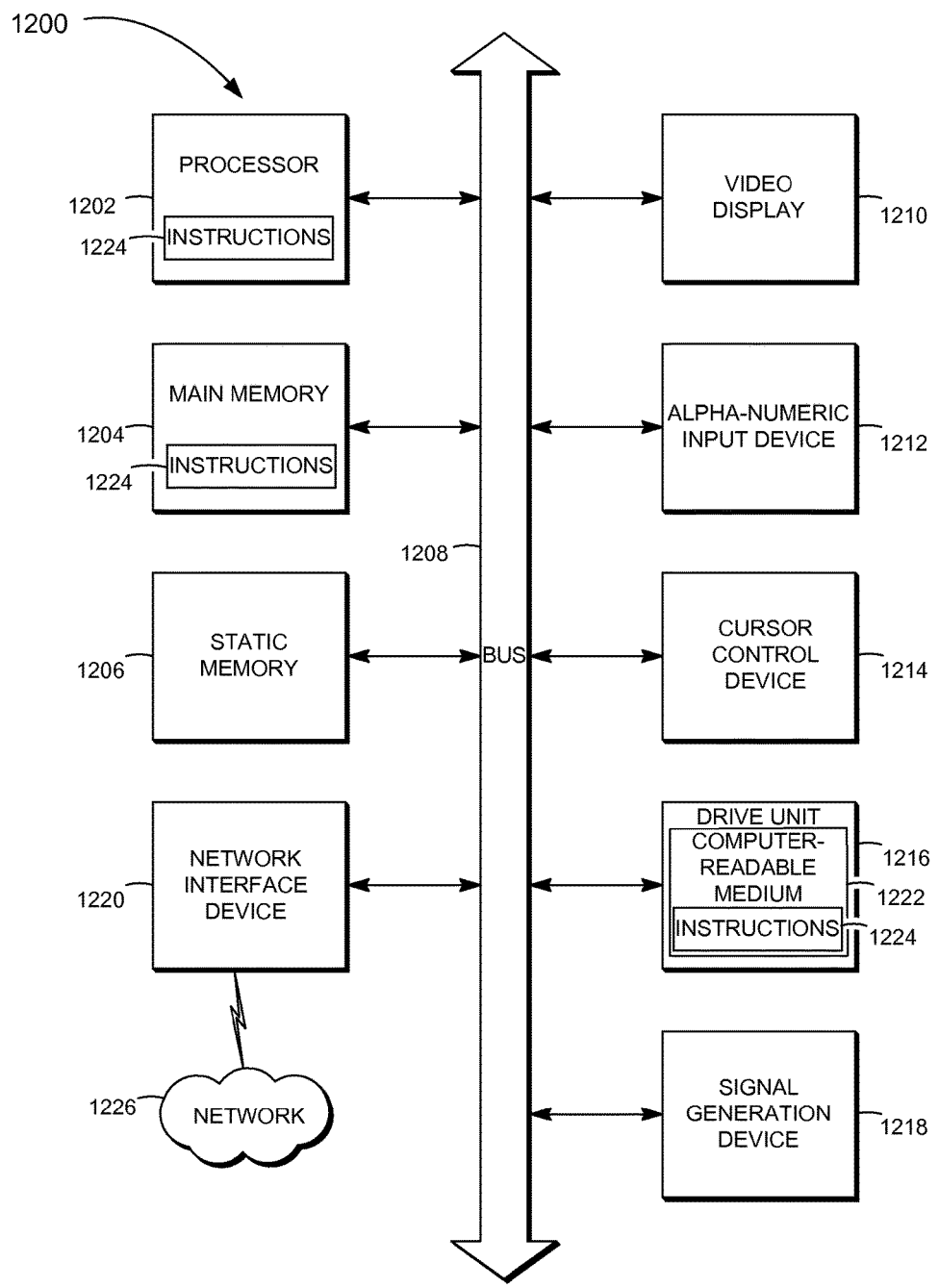
FIG. 12 is a block diagram of a machine in the example form of a computer system within which a set of instructions for causing the machine to perform any one or more of the methodologies discussed herein may be executed or stored.

FIG. 12 shows a block diagram of a machine in the example form of a computer system 1200 within which a set of instructions may be executed causing the machine to perform any one or more of the methods, processes, operations, or methodologies discussed herein. The prescriber device 102, the benefit manager device 106, and/or the pharmacy device 108 may include the functionality of the one or more computer systems 1200.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1200 includes a processor 1202 (e.g., a central processing unit (CPU) a graphics processing unit (GPU) or both), a main memory 1204 and a static memory 1206, which communicate with each other via a bus 1208. The computer system 1200 further includes a video display unit 1120 (e.g., a liquid crystal display (LCD) or a cathode ray tube (CRT)). The computer system 1200 also includes an alphanumeric input device 1212 (e.g., a keyboard), a cursor control device 1214 (e.g., a mouse), a drive unit 1216, a signal generation device 1218 (e.g., a speaker) and a network interface device 1220.

The drive unit 1216 includes a computer-readable medium 1222 on which is stored one or more sets of instructions (e.g., software 1224) embodying any one or more of the methodologies or functions described herein. The software 1224 may also reside, completely or at least partially, within the main memory 1204 and/or within the processor 1202 during execution thereof by the computer system 1200, the main memory 1204 and the processor 1202 also constituting computer-readable media.

The software 1224 may further be transmitted or received over a network 1226 via the network interface device 1220.

While the computer-readable medium 1222 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Unless clearly and explicitly identified otherwise, the terms "member" and "device operator" are frequently used interchangeably herein.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a prescription request is received for a prescription drug. The prescription drug is associated with a prescription. A determination that the prescription drug is a controlled substance is made. Pharmacy claims data is analyzed to determine whether past claims adjudication data is associated with a patient controlled substance identifier. The patient controlled substance identifier is associated with a patient that has been prescribed the prescription drug through the prescription without identifying the patient as being a member of a benefit manager. The prescription request is evaluated based on a determination that the past claims adjudication data is associated with the patient controlled substance identifier. A notification is generated based on evaluation of the prescription request.

In an example embodiment, a prescription request for a prescription drug is received. The prescription drug is associated with a prescription. A determination of whether the prescription meets controlled substance criteria is made. The controlled substance criteria includes that the prescription drug is a controlled substance and the patient has not provided a member identifier that identifies the member as being a member of a benefit manager. An evaluation of the prescription request is made based on a determination that the prescription meets the controlled substance criteria. A notification is generated based on evaluation of the prescription request.

In an example embodiment, receipt of a prescription associated with a controlled substance is recorded. Member non-identification is recorded. The member non-identification reflects that a patient associated with the prescription is not being identified as a member of a benefit manager. An adjudication request for the controlled substance is transmitted based on recordation of the member non-identification. A response to transmission of the adjudication request is received.

In an example embodiment, prescription information including selection of a controlled substance for a patient is transmitted. The prescription information does not include a member identifier that identifies the patient as being a member of a benefit plan provided through a benefit manager. Drug interaction information associated with the patient is received in response to transmission of the prescription information. The drug interaction information is not based on identification of the patient as being a member of the benefit plan provided through the benefit manager.

Thus, methods and systems for drug interaction review have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

While the methods and systems generally describe a drug interaction review for controlled substance, the methods and system may be used to perform one or more parts of DUR may be performed where a patient pays cash or otherwise fails to identify himself or herself as having a member identifier.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
receiving over a network, on a benefit manager device, a prescription request for a prescription drug from at least one of a prescriber device and a pharmacy device, the prescription drug being associated with a prescription;
determining, on the benefit manager device, that the prescription drug is a controlled substance;
determining, on the benefit manager device, that a patient for whom the prescription drug was prescribed has not provided a member identifier of a drug benefit plan;
associating, on the benefit manager device, the prescription request with a controlled substance identifier, wherein the controlled substance identifier is also associated with the prescription drug, wherein the controlled substance identifier is generated based on a prescriber associated with the prescription, a pharmacist associated with the prescription, a pharmacy associated with the prescription, a cash identifier associated with the prescription, a timing associated with the prescription, or combinations thereof, and wherein the controlled substance identifier is not generated based on patient identification information;
analyzing, on the benefit manager device, pharmacy claims data to determine whether past claims adjudication data is associated with the controlled substance identifier, the past claims adjudication data associated with the controlled substance identifier also does not include the patient identification information;
evaluating, on the benefit manager device, the prescription request to determine whether the past claims adjudication data associated with the controlled substance identifier indicates that the prescription drug has been dispensed in a claim associated with the controlled substance identifier within a predetermined time of the prescription request;
generating, on the benefit manager device, a notification based on evaluation of the prescription request;
transmitting the notification from the benefit manager device via the network to at least one of the pharmacy device and the prescriber device, the notification indicating whether to dispense or not dispense the prescription drug; and
dispensing the prescription drug when the notification indicates to dispense the prescription drug.

2. The method of claim 1, further comprising:
generating the controlled substance identifier,
wherein analysis of the pharmacy claims data is performed based on generation of the controlled substance identifier and receipt of the prescription request.

3. The method of claim 1, further comprising:
determining that the prescription request is associated with a cash purchase of the prescription drug,
wherein analysis of the pharmacy claims data is in response to a determination that the prescription request is associated with the cash purchase.

4. The method of claim 3, further comprising:
selecting cash purchase pharmacy claims data among the pharmacy claims data based on a determination that the prescription request is associated with the cash purchase,
wherein analysis of the pharmacy claims data is performed on the cash purchase pharmacy claims data to determine whether the past claims adjudication data is associated with the controlled substance identifier.

5. The method of claim 1, wherein analyzing the pharmacy claims data comprises:
selecting the past claims adjudication data from the pharmacy claims data based on a time criterion; and
determining whether the past claims adjudication data is associated with the controlled substance identifier.

6. The method of claim 1, further comprising:
transmitting a response based on the notification.

7. The method of claim 1, wherein the prescription request is an adjudication request to adjudicate the prescription for the patient, and wherein evaluating the prescription request includes performing a drug interaction review on the prescription drug based on the past claims adjudication data.

8. The method of claim 7, further comprising:
identifying a past prescription associated with the past claims adjudication data,
wherein performance of the drug interaction review for the prescription drug is based on the past prescription.

9. The method of claim 7, wherein performance of the drug interaction review is performed as part of performing a drug utilization review (DUR) for the prescription drug based on the past claims adjudication data.

10. The method of claim 7, further comprising:
recording payment to a pharmacy based on receipt of the adjudication request.

11. The method of claim 1, wherein the prescription includes the controlled substance identifier.

12. The method of claim 1, wherein the past claims adjudication data does not include indicium that directly identifies the patient.

13. The method of claim 1, wherein the notification includes an amount to be paid to a pharmacy based on dispensing of the prescription drug.

14. A method comprising:
receiving, over a network, on a benefit manager device, a prescription request for a prescription drug from at least one of a prescriber device and a pharmacy device, the prescription drug being associated with a prescription;
determining, on the benefit manager device, whether the prescription meets controlled substance criteria, the controlled substance criteria including that the prescription drug is a controlled substance and a patient has not provided a member identifier that identifies a member of a benefit manager;
associating, on the benefit manager device, the prescription request with a controlled substance identifier, wherein the controlled substance identifier is also associated with the prescription drug, and wherein the controlled substance identifier is based on a prescriber associated with the prescription, a pharmacist associated with the prescription, a pharmacy associated with the prescription, a cash identifier associated with the prescription, a timing associated with the prescription, or combinations thereof, and wherein the controlled substance identifier is not based on patient identification information;
analyzing, on the benefit manager device, pharmacy claims data to determine whether past claims adjudication data is associated with the controlled substance identifier, the past claims adjudication data associated with the controlled substance identifier also does not include the patient identification information;
evaluating, on the benefit manager device, the prescription request to determine whether the past claims adjudication data associated with the controlled substance identifier indicates that the prescription drug has been dispensed in a claim associated with the controlled substance identifier within a predetermined time of the prescription request;
generating, on the benefit manager device, a notification based on evaluation of the prescription request;
transmitting the notification from the benefit manager device via the network to at least one of the pharmacy device and the prescriber device, the notification indicating whether to dispense or not dispense the prescription drug; and
dispensing the prescription drug when the notification indicates to dispense the prescription drug.

15. The method of claim 14, wherein the prescription request is an adjudication request to adjudicate the prescription for the patient, and wherein evaluating the prescription request includes performing a drug interaction review on the prescription drug based on the determination that the prescription meets the controlled substance criteria.

16. A non-transitory machine-readable medium comprising instructions, which, when executed by one or more processors, cause the one or more processors to perform the following operations:
receive, over a network on a benefit manager device, a prescription request for a prescription drug from at least one of a prescriber device and a pharmacy device, the prescription drug being associated with a prescription;
determine, on the benefit manager device, that the prescription drug is a controlled substance;
determine, on the benefit manager device, that a patient for whom the prescription drug was prescribed has not provided a member identifier of a drug benefit plan;
associate, on the benefit manager device, the prescription request with a controlled substance identifier, wherein the controlled substance identifier is also associated with the prescription drug, and wherein the controlled substance identifier is generated based on a prescriber associated with the prescription, a pharmacist associated with the prescription, a pharmacy associated with the prescription, a cash identifier associated with the prescription, a timing associated with the prescription, or combinations thereof, and wherein the controlled substance identifier is not generated based on patient identification information;
analyze, on the benefit manager device, pharmacy claims data to determine whether past claims adjudication data is associated with the controlled substance identifier, the past claims adjudication data associated with the controlled substance identifier also does not include the patient identification information;
evaluate, on the benefit manager device the prescription request to determine whether the past claims adjudication data associated with the controlled substance identifier indicates that the prescription drug has been dispensed in a claim associated with the controlled substance identifier within a predetermined time of the prescription request;
generate, on the benefit manager device a notification based on evaluation of the prescription request;
transmit the notification from the benefit manager device via the network to at least one of the pharmacy device and the prescriber device, the notification indicating whether to dispense or not dispense the prescription drug; and
cause a pharmacy to dispense the prescription drug when the notification indicates to dispense the prescription drug.

17. A non-transitory machine-readable medium comprising instructions, which, when executed by one or more processors, cause the one or more processors to perform the following operations:
receive, over a network on a benefit manager device, a prescription request for a prescription drug from at least one of a prescriber device and a pharmacy device, the prescription drug being associated with a prescription;

determine, on the benefit manager device, whether the prescription meets a controlled substance criteria, the controlled substance criteria including that the prescription drug is a controlled substance and a patient has not provided a member identifier that identifies a member of a benefit manager;

associate, on the benefit manager device, the prescription request with a controlled substance identifier, wherein the controlled substance identifier is also associated with the prescription drug, and wherein the controlled substance identifier is generated based on a prescriber associated with the prescription, a pharmacist associated with the prescription, a pharmacy associated with the prescription, a cash identifier associated with the prescription, a timing associated with the prescription, or combinations thereof, and wherein the controlled substance identifier is not generated based on patient identification information;

analyze, on the benefit manager device, pharmacy claims data to determine whether past claims adjudication data is associated with the controlled substance identifier, the past claims adjudication data associated with the controlled substance identifier also does not include the patient identification information;

evaluate, on the benefit manager device, the prescription request to determine whether the past claims adjudication data associated with the controlled substance identifier indicates that the prescription drug has been dispensed in a claim associated with the controlled substance identifier within a predetermined time of the prescription request;

generate, on the benefit manager device, a notification based on evaluation of the prescription request; and transmit the notification from the benefit manager device via the network to at least one of the pharmacy device and the prescriber device, the notification indicating whether to dispense or not dispense the prescription drug; and cause a pharmacy to dispense the prescription drug when the notification indicates to dispense the prescription drug.

\* \* \* \* \*